(12) United States Patent
Suffritti et al.

(10) Patent No.: US 9,216,248 B2
(45) Date of Patent: Dec. 22, 2015

(54) METHOD AND A DEVICE FOR MONITORING A STATE OF A BLOOD LINE IN A MACHINE FOR EXTRACORPOREAL BLOOD TREATMENT

(75) Inventors: Mauro Suffritti, Medolla (IT); Marco Lizzi, Vigarano Mainarda (IT)

(73) Assignee: Gambro Lundia AB, Lund (SE)

( * ) Notice: Subject to any disclaimer, the term of this patent is extended or adjusted under 35 U.S.C. 154(b) by 406 days.

(21) Appl. No.: 13/643,724

(22) PCT Filed: Apr. 22, 2011

(86) PCT No.: PCT/IB2011/000883
§ 371 (c)(1),
(2), (4) Date: Oct. 26, 2012

(87) PCT Pub. No.: WO2011/135427
PCT Pub. Date: Nov. 3, 2011

(65) Prior Publication Data
US 2013/0046226 A1    Feb. 21, 2013

(30) Foreign Application Priority Data
Apr. 28, 2010  (EP) .................................. 100004477

(51) Int. Cl.
*G08B 21/00* (2006.01)
*A61M 1/36* (2006.01)
*A61M 1/16* (2006.01)

(52) U.S. Cl.
CPC .............. *A61M 1/3639* (2013.01); *A61M 1/16* (2013.01)

(58) Field of Classification Search
CPC ....................................................... A61M 1/00
USPC ............. 340/573.1, 606, 608; 604/4.01, 6.16, 604/48, 65, 131; 702/50
See application file for complete search history.

(56) References Cited

U.S. PATENT DOCUMENTS

| | | | |
|---|---|---|---|
| 5,906,589 | A | 5/1999 | Gordon et al. |
| 6,623,443 | B1 | 9/2003 | Polaschegg |
| 2002/0174721 | A1 | 11/2002 | Gross |
| 2005/0284815 | A1 | 12/2005 | Sparks et al. |
| 2009/0292236 | A1 | 11/2009 | Kleinekofort |

FOREIGN PATENT DOCUMENTS

| | | |
|---|---|---|
| DE | 3720664 | 1/1989 |
| DE | 102006032815 | 1/2008 |
| DE | 102008015832 | 10/2009 |
| EP | 1584339 | 10/2005 |
| EP | 1 930 035 | 6/2008 |
| JP | 3-193059 | 8/1991 |
| WO | 2008/135193 | 11/2008 |
| WO | 2009156174 A2 | 12/2009 |

OTHER PUBLICATIONS

"Schule 2000 Grundstock des Wissens: für die Sekundarstufen I und II. Zusammenhänge erkennen, Fakten nachschlagen, Prüfungen vorbereiten". Serges Medien GmbH, 1999. pp. 1-3, 292-293.
European Search Report completed Aug. 19, 2011.

*Primary Examiner* — Jeffery Hofsass
(74) *Attorney, Agent, or Firm* — K&L Gates LLP

(57) ABSTRACT

A method for monitoring a state of a blood line in a circuit for extracorporeal blood treatment, including the steps of: acquiring at least a first pressure value from a first sensor mounted at a first point of a circuit for extracorporeal blood treatment, comprising a blood line in which the blood is subjected to a pulsating thrust; acquiring at least a second pressure value from a second sensor mounted at a second point, distinct from the first point of the blood line of the circuit for extracorporeal blood treatment, and correlating at least a first value, correlated to the first pressure value, and at least a second value, correlated to the second pressure value, with at least a threshold value, in order to obtain a datum representing a state of the blood line.

44 Claims, 12 Drawing Sheets

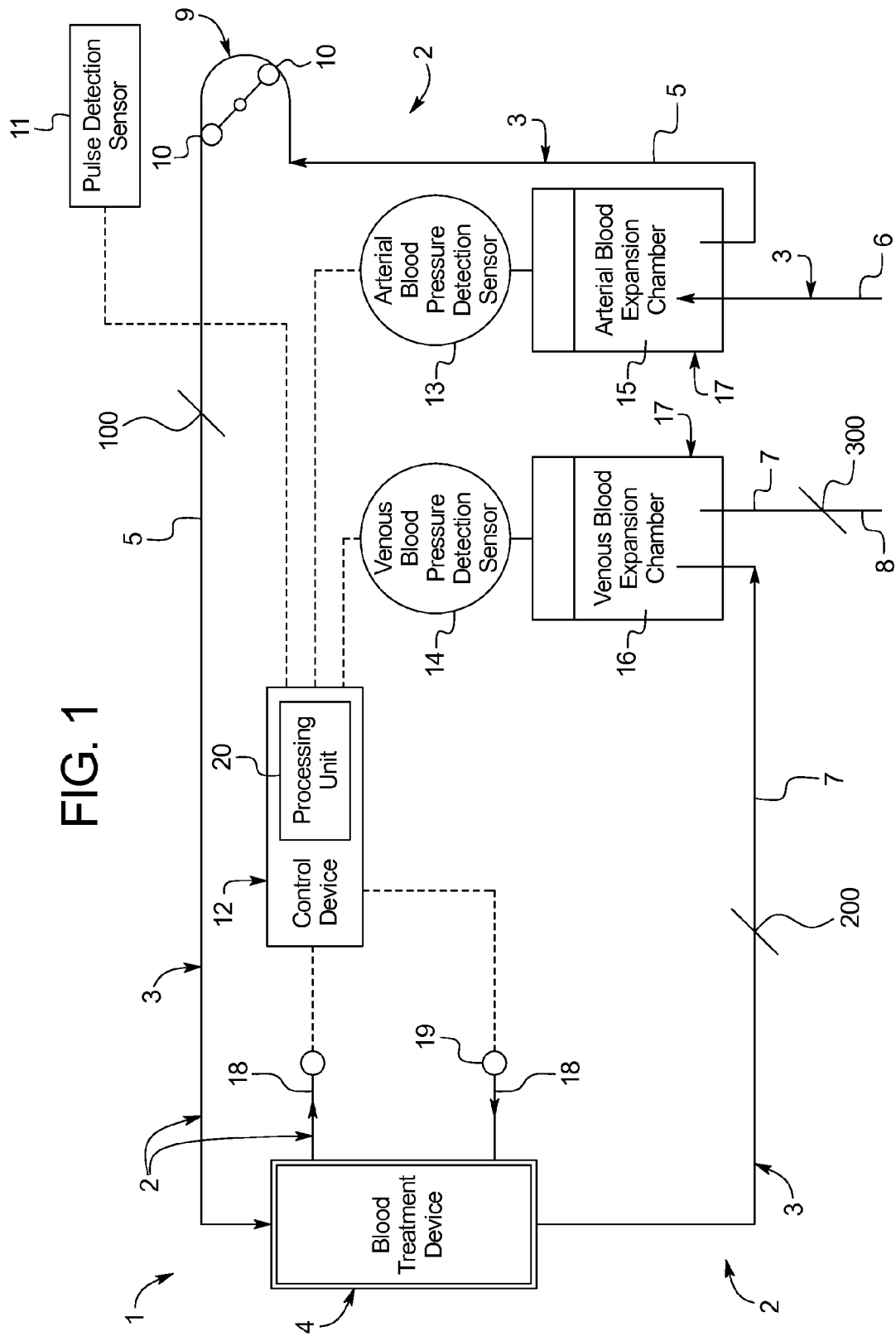

METHOD AND A DEVICE FOR MONITORING A STATE OF A BLOOD LINE IN A MACHINE FOR EXTRACORPOREAL BLOOD TREATMENT

TECHNICAL FIELD

The invention relates to a method and a corresponding device for monitoring a state of a blood line in a machine for extracorporeal blood treatment. Specifically, though not exclusively, the invention is applied in the medical field for monitoring the state of extracorporeal medical liquid and/or biological fluid flows. For example the invention can be applied in a hemodialysis or hemo(dia)filtration apparatus for detecting presence of any partial or total stenosis and occlusions in the blood removal line and/or return to or from a patient. A method and a device of the invention can also be applied in further applicational fields not described in detail in the present description.

BACKGROUND OF THE INVENTION

It is known that many fluid systems require precise measurement of the state of the system, and in particular various properties and/or parameters of the fluids flowing through them. In some of these systems measurements of single parameters are important. In other cases, the change or difference of parameters is important. In both cases the accuracy required for each particular fluid system can vary on the basis of the particular fluid or fluids involved, and/or on the basis of the aim of the system.

An example of a fluid system having special requisites which can be considerably influenced by the accuracy of the parametric measurements, in particular comprising the determinations of the pressure, is a blood flow system that is external of the body, also known as an extracorporeal blood system.

An extracorporeal blood system normally includes a device for blood treatment flowing internally thereof. There are various types of these devices. Filtration devices having semipermeable membranes are commonly used in extracorporeal blood systems such as those used for dialysis or for therapeutic plasmapheresis (TPE). The primary aim of a semipermeable membrane is normally to provide removal or separation of determined elements or components from blood. Urea and other waste products are removed from the blood during dialysis, and the blood plasma is separated from the red corpuscles during TPE. The blood or the red corpuscles processed are then returned to the patient.

In more detail, in an extracorporeal blood system using a semipermeable membrane device, the process is the following. The blood is removed from the patient, passed along a side of a semipermeable membrane and in contact therewith. Undesired portions of the blood (urea in the case of dialysis, plasma in the case of TPE) diffuse or are filtered through the pores of the semipermeable membrane. The blood remaining on the blood side of the semipermeable membrane is then returned to the patient with a smaller quantity of the undesired substances.

As mentioned herein above, the prior art describes monitoring the state of the blood lines of medical machines for extracorporeal blood treatment, for example for detecting the presence of any eventual stenoses, i.e. narrowings in the lines in which the blood runs, either partial or total, or other occlusions. The stenoses can be due to various causes, from a progressive coagulation of the blood to a narrowing due to accidental clamping of the line, a blockage in a blood treatment device arranged in the bloodline, or other causes. For example, document U.S. Pat. No. 6,623,443 describes a method for detecting stenoses in a blood access or in a line for extracorporeal blood treatment which comprises monitoring the amplitude of an oscillating pressure signal in the circuit itself and detecting the presence of eventual stenoses on the basis of a monitoring of the variations in the amplitude. This method can be performed with a control device that is not very complex, but enables detection of the presence of stenoses only after the stenoses have caused a significant variation in a pressure measured in the circuit.

This method therefore does not entirely prevent the risk of damage to some components of the circuit, or deterioration of the blood (hemolysis) in the case of stenosis, as the reaction time of the control device can in some cases be not sufficiently rapid, also because there can sometimes be sufficient pressure variations for brief periods of time to damage the blood or some components. Document US2002/0174721 describes another method for detecting stenoses in lines for extracorporeal blood treatment. The method comprises measuring an oscillating pressure signal, for example due to the thrust of the blood by a peristaltic pump, and to perform a frequency analysis of the oscillating pressure signal in order to detect the presence of a stenosis in a case of attenuation of the components of greater frequency of the signal. The method enables a more prompt detection of the presence of stenosis with respect to the previously-cited method, before the pressure variations due to the presence of the stenosis can take on relevant values that might be potentially dangerous for the blood line and for the blood. The method however requires a sophisticated and expensive control device, which is able to perform complex calculation, such as frequency analysis of a signal in real time.

Both the above-described methods further require the presence of a high number of pressure sensors in the extracorporeal blood treatment circuit, in order to detect the changes in pressures in the various parts of the circuit, with a consequent increase in the complexity and costs of the system. Further, these methods essentially allow only verification of stenoses in the blood line, while not enabling detection of further significant parameters relating to the functioning state of the extracorporeal blood circuit.

SUMMARY OF THE INVENTION

An aim of the present invention is to make available a method and a corresponding device for monitoring the state of a blood line in a machine for extracorporeal blood treatment, which obviate the drawbacks of the prior art.

A further aim of the present invention is to realise a method and a corresponding device for monitoring the state of a blood line in a machine for extracorporeal blood treatment which readily signals the presence of partial or total stenoses in the blood line.

A further aim of the present invention is to realise a method and a corresponding device for monitoring the state of a blood line in a machine for extracorporeal blood treatment which further enable obtaining an index that is representative of further qualities of the functioning of the blood line, such as for example the presence of an excessive quantity of air in the dialysis filter or an evaluation of the risk of blood coagulation.

A further aim of the present invention is to make available a method and a corresponding device for monitoring the state of a blood line in a machine for extracorporeal blood treatment which provide a high safety level against damage to the components of the blood line and against deterioration of the blood passing through the line.

A further aim of the present invention is to realise a method and a corresponding device for monitoring the state of a blood line in a machine for extracorporeal blood treatment which enable detection of the presence of stenoses in various parts of the blood line, using a reduced number of sensors.

A further aim of the present invention is to realise a method and a corresponding device for monitoring the state of a blood line in a machine for extracorporeal blood treatment which are able to function using the sensors normally present in the blood line, without requesting additional sensors.

A further aim of the present invention is to realise a method for monitoring the state of a blood line in a machine for extracorporeal blood treatment which is reliable and precise, which can be actuated simply, and which does not require excessively complex and expensive control devices in order to be actuated.

A further aim of the present invention is make available a device for monitoring the state of a blood line in a machine for extracorporeal blood treatment which exhibits a simple structure, which is economical, reliable and compact in size.

At least one of the above-indicated aims is attained by a method and a corresponding device for monitoring the state of a blood line in a machine for extracorporeal blood treatment as in one or more of the appended claims, taken singly or in any combination.

In a further aspect, the invention relates to a method for detecting a state of partial or total stenosis in a blood line in a machine for extracorporeal blood treatment, in agreement with any one of the appended method claims or of the aspects described herein, comprising the step of emitting a signal, in particular an alarm signal, corresponding to a predetermined value of the information representing a state of partial or total stenosis in the extracorporeal blood circuit.

In a further aspect, the invention relates to a method, as in any one of the appended method claims or the aspects indicated herein, further comprising a step of emitting an alarm signal and/or arresting the functioning of the pump in the circuit, in the presence of a condition of partial or total stenosis in the blood line.

In a further aspect, the invention relates to a method, in agreement with any one of the appended method claims or to aspects indicated herein, in which a first pressure value and a second pressure value are read at a same moment at two distinct points in the circuit.

In a further aspect, the invention relates to a method, in agreement with any one of the appended method claims or to aspects indicated herein, in which the time interval corresponds to a step of the relative pressure impulse signals.

In a further aspect, the invention relates to a method, in accordance with any one of the appended method claims or aspects indicated herein, in which the step of emitting a representative signal of a partial or total stenosis in the blood line is carried out on verification of a predetermined result in at least two successive comparisons between pressure values calculated in successive temporal intervals.

In a further aspect, the invention relates to a method, in accordance with any one of the appended method claims or aspects indicated herein, comprising a step of further comparison between at least one of the first pressure value and/or the second pressure value with corresponding threshold values and in which the step of emitting the signal representing a partial or total stenosis is carried out at a predetermined result of the step of further comparison.

In a further aspect, the invention relates to a method for detecting partial or total stenoses in a blood line of a machine for extra-corporeal blood treatment, comprising steps of acquiring at least a first pressure value from an arterial blood pressure sensor in an arterial blood removal line from a patient, being part of a blood line in which the blood is subject to a pulsating thrust, acquiring at least a second pressure value from a venous blood pressure sensor in a venous blood return line to a patient, being part of the blood line, comparing at least a first value for the first pressure value measured in a predetermined temporal interval and at least a second value measured in the predetermined temporal interval, and emitting a signal representing a partial or total stenosis in the blood line on receiving a predetermined result from the comparison between the values.

In a further aspect, the invention relates to a method for detecting partial or total stenoses in a blood line in a machine for extracorporeal blood treatment, comprising steps of acquiring at least a first pressure value from a first pressure sensor of a treatment fluid mounted in a hydraulic circuit for a blood treatment fluid, comprising a blood treatment device arranged in a blood line in which the blood is subject to a pulsating thrust, acquiring at least a second pressure value from a venous blood pressure sensor in a blood return line to the patient, being part of the blood line, comparing at least a change in the first pressure value in at least two successive temporal instants, and emitting a signal representing a partial or total stenosis in the blood line on obtaining a predetermined result from the comparison of the changes.

In a further aspect, the invention relates to a method for detecting partial or total stenoses in a blood line in a machine for extracorporeal blood treatment, comprising steps of acquiring at least a first pressure value from a first pressure sensor of a treatment fluid mounted in a hydraulic circuit for a blood treatment fluid, comprising a blood treatment device arranged in a blood line in which the blood is subject to a pulsating thrust, acquiring at least a second pressure value from a venous blood pressure sensor in a venous blood return line to a patient, being part of the blood line, comparing at least a change in the first pressure value between at least two successive temporal instants with a relative threshold value, comparing at least a change in the first pressure value between at least two successive temporal instants with a relative threshold value, comparing at least a change in the second pressure value between at least two successive temporal instants with a further relative threshold value, and emitting a signal representing a partial or total stenosis in the blood line on receiving predetermined results in the steps of comparing the variations in the first and the second pressure value.

In a further aspect, the invention relates to a method for detecting partial or total stenoses in a blood line of a machine for extracorporeal blood treatment, comprising steps of acquiring at least a first pressure value from an arterial blood pressure sensor in an arterial blood removal line from a patient, being part of a blood line in which the blood is subjected to a pulsating thrust and comparing at least a change in the pressure value between at least two successive temporal instants and a relative threshold value, and emitting a signal representing a partial or total stenosis in the blood line on calculating a predetermined result during the step of comparing the change in the first pressure value.

In a further aspect, the signal representing a partial or total stenosis in the blood line is emitted in a case in which the change in the first pressure value is lower than a predetermined decrease threshold value.

In a further aspect, the invention relates to a software program destined to operate in a control device of blood lines of extracorporeal circuits in medical machines for actuating a method in accordance with any one of the claims or the aspects cited herein above.

In a further aspect, the invention relates to a control device for detecting stenoses in blood lines of medical machines, in accordance with any one of the accompanying device claims or the aspects indicated herein, comprising at least a processing unit which can be connected to a plurality of pressure sensors of a fluid or blood in an extracorporeal blood circuit of a medical machine and is configured to actuate a method in accordance with the invention.

In a further aspect, the invention relates to an apparatus, in accordance with any one of the appended apparatus claims or the aspects indication herein, in which the first sensor mounted is mounted at the first point of the blood line.

In a further aspect, the invention relates to an apparatus, in accordance with any one of the appended apparatus claims or any aspect indicated herein, in which the first sensor mounted is mounted at the first point of a hydraulic circuit for a blood treatment fluid.

In a further aspect, the invention relates to an apparatus, in accordance with any one of the appended apparatus claims or the aspects indicated herein, in which an arterial pressure detecting sensor of the blood is mounted in an arterial blood expansion chamber and a venous pressure-detecting sensor is mounted in a venous blood expansion chamber.

Further characteristics and advantages of the present invention will more clearly emerge from the detailed description that follows, of at least an embodiment of the invention, illustrated purely by way of non-limiting example in the accompanying figures of the drawings.

BRIEF DESCRIPTION OF THE DRAWINGS

The detailed description that follows herein below is made with reference to the accompanying figures of the drawings, provided by way of non-limiting example, in which:

FIG. 1 is a schematic view, in accordance with at least an embodiment of the present invention, of a blood line being part of an apparatus for extracorporeal blood treatment via a hemodialysis treatment (HD);

DETAILED DESCRIPTION

Figure 2A:
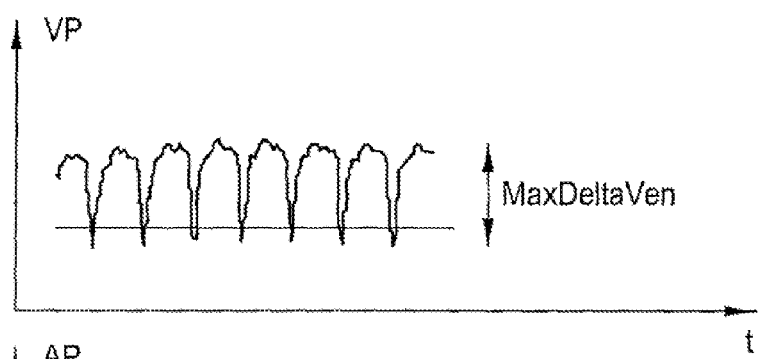
FIGS. 2a and 2b respectively illustrate a possible time progression of a venous pressure value and an arterial pressure value measured in the blood line of FIG. 1.

With reference to the figures of the drawings, 1 denotes in its entirety an apparatus 1 for extracorporeal blood treatment comprising at least a circuit 2 for extracorporeal blood treatment comprising having at least a blood line 3 and a blood treatment device 4, for example a dialyser having a semipermeable membrane internally thereof. In particular the circuit 2 illustrated is suitable for performing at least a hemodialysis treatment (HD). The blood line 3 comprises at least an arterial line 5 destined to carry blood from an arterial access 6 of a patient to the blood treatment device and at least a venous line 7 destined to return the blood from the blood treatment device 4 to a venous access 8 of the patient.

The apparatus 1 further comprises at least a peristaltic pump 9 for the blood mounted in the extracorporeal circuit 2 in order to pump the blood at a thrust pressure having a pulsating action over time. The peristaltic pump 9 is mounted along the arterial line 5.

In general a control unit 12 has an information at least relating to the APP pulse of the peristaltic pump 9. In particular the information is used to synchronize the values used for the implementation of the method herewith described and in detail it is a timing information.

This information may be obtained using for example a step motor and knowing in each instant the position of the peristaltic pump 9 (i.e. of the rotor of the pump).

The peristaltic pump 9 provided with a rotor 10 (and at least one magnet or at least two magnets and more generally a prefixed number of magnets) is provided with a sensor 11 for detecting the pulse APP of the peristaltic pump 9.

In general the sensor 11 is able to detect the APP pulse of the peristaltic pump 9 and may be any kind of sensor capable of performing the above detection.

For example the pulse-detecting sensor 11 is able to detect the passage of the magnet/magnets on the rotor 10 of the pump 9, such as to be able to provide a control device 12 with a time signal corresponding to each rotation (or half rotation) of the rotor 10 of the peristaltic pump 9.

Of course using an appropriate number of magnets/sensors it is possible to detect any angular position of the rotor (any kind of degree of rotation).

The pulse-detecting sensor can be a Hall-effect type sensor for detecting the passage of the rotor 10.

In the following description reference will be made to the Hall sensor even though any of the above mentioned solutions can be used as an alternative or in combination.

The apparatus 1 further comprises at least an arterial blood pressure detection sensor 13 mounted in a first point of the extracorporeal circuit 2 upstream of the pump 9 and at least a venous blood pressure detection sensor 14 mounted in a second point of the extracorporeal circuit 2 downstream of the pump 9. Note that both the arterial pressure AP and the venous pressure VP measured by the relative sensors exhibit, in normal functioning conditions of the extracorporeal blood treatment circuit 2, a pulsating action, due to the thrust on the blood imparted by the peristaltic pump 9. In the present description, by the expression "pulsating" is meant a periodic action characterised by a substantial oscillation between a maximum value and a minimum value, whatever the form of the oscillation, which is influenced by various factors, among which the characteristics of the blood line 3 and the components mounted thereon.

The arterial blood pressure detection sensor 13 is mounted in an arterial blood expansion chamber 15, arranged along the arterial line 5, and the venous blood pressure detection sensor 14 is mounted in a venous blood expansion chamber 16 arranged along the venous line 7. The arterial expansion chamber and the venous expansion chamber are housed internally of a blood cassette 17 of known type and thus not further described herein.

The apparatus 1 further comprises a hydraulic circuit 18 for a blood treatment fluid operatively connected to the treatment device 4 and at least a pressure detector sensor 19 of the treatment fluid pressure mounted in the hydraulic circuit or in the treatment device 4.

The apparatus 1 further comprises a control device 12 of the state of the blood line 3, and in particular for the detection of stenoses in the blood line, in accordance with the invention.

The control device 12 comprises at least a processing unit 20 which is connectable to a plurality of pressure sensors of a fluid or blood in the extracorporeal blood treatment circuit 2. Of importance is the fact that both the control unit 12 and the processing unit 20 might be in themselves of conventional type, as also could be the corresponding elements already present in the known apparatus, but in the present case they are configured to perform the steps of the method of the present invention. Also of importance is the fact that the various pressures measured in the circuit are sampled at a frequency, for example with a measurement every 20 ms (and therefore greater than that of the revolution of the rotor 10 of the peristaltic pump 9), such that the control unit can receive various measurements of the pressures provided by the various sensors for each revolution of the rotor 10 of the peristaltic pump 9.

The control unit is configured to actuate a method in accordance with the invention. The control unit 12 can in particular be configured to detect stenoses in blood lines of medical machines. The control device is operatively connected at least to the arterial pressure detection sensor 13, to the venous pressure detecting sensor 14 and to the treatment fluid pressure detection sensor 19, and is configured to carry out a method of the invention with the corresponding pressure signals acquired by the cited sensors.

A monitoring method of a state of a blood line 3 in a machine for extracorporeal blood treatment comprises steps of: acquiring at least a first pressure value from a first sensor 13, 19 mounted at a first point of a blood line in which the blood is subjected to a pulsating thrust or in a hydraulic circuit 18 for a blood treatment fluid; acquiring at least a second pressure value from a second sensor 14 mounted at a second point distinct from the first point of the blood line and correlating at least a first value, correlated to the first pressure value, and at least a second value, correlated to the second pressure value, with at least a threshold value in order to obtain a representative datum of a state of the blood line 3.

The method further comprises a step of emitting a signal representing the state of the blood line 3 when a predetermined alarm value is reached for information representing a state, and in particular on obtaining a predetermined value of the representative information of a state of partial or total stenosis in the extracorporeal blood treatment circuit. The step of emitting a signal representing the state of the blood line 3 can be performed on obtaining a predetermined value of the information for a predetermined number of consecutive times in a predetermined number of successive temporal instants, for example after a predetermined number of cycles of the peristaltic pump 9 measured by the pulse detecting sensor 11 of the pump 9.

The method can be in particular destined to detect a state of partial or total stenosis of a blood line 3 in a machine for extracorporeal blood treatment, and in this case can comprise a step of emitting a signal corresponding to a predetermined value of the information representing a state of partial or total stenosis in the extracorporeal blood treatment circuit 2.

The method can further comprise a step of emitting an alarm signal in the presence of a partial or total stenosis condition in the blood line 3. In the method of the invention the first pressure value and the second pressure value can be detected at a same temporal instant.

The method can comprise states of acquiring a plurality of first pressure values and a plurality of second pressure values, the first and second pressure values being sampled and detected at a plurality of corresponding successive temporal instants and distanced from one another by a predetermined temporal instant. The step of comparing at least a first value correlated to the first pressure value and at least a second value correlated to a least a second pressure value with at, least a threshold value for obtaining a datum representing a step of the blood line 3 can be carried out only at a specific angular position of a rotor 10 of the peristaltic pump 9 mounted in the circuit. The first value and the second value can be correlated to corresponding amplitudes of pulsating signals respectively of the first pressure value and the second pressure value, the amplitudes being calculated by detecting the pressure values from the first and the second sensor at corresponding predetermined time intervals. The time interval can correspond to a step of the respective pressure pulse signals. The first value and the second value are respectively correlated to corresponding differences between two first pressure values measured by the first sensor 13, 19 at two successive temporal and distinct instants and between two second pressure values measures by the second sensor in the two successive and distinct temporal instants.

The method can comprise a step of calculating at least a relationship between the first value and the second value and a step of comparing the result of the relationship with a threshold value for obtaining information relating to a step of the blood line 3.

The method can comprise a step of performing at least a subtraction between the first value and the second value and comparing the result of the subtraction with a threshold value in order to obtain information relating to a state of the blood line 3.

The method can further comprise a step of individually comparing the first value and the second value with respective threshold values in order to obtain information relating to a state of the blood line 3.

The method can comprise steps of calculating at least two first values, distinct from one another, and correlated differently to the first pressure value and/or at least two second values distinct from one another and differently correlated to the second pressure value and the steps of correlating the two first values with respective threshold values and/or the two second values with respective threshold values for obtaining information relating to a state of the blood line 3.

The first pressure value can be measured by means of a first sensor mounted at an arterial expansion chamber of the blood line and the second pressure value can be measured by means of a second sensor 14 mounted at a venous expansion chamber of the blood line, a peristaltic pump 9 being interposed between the arterial chamber 15 and the venous chamber 16 in order to produce the pulsating thrust of the blood. The first pressure value can be measured by means of a first sensor mounted at a hydraulic circuit 18 for a blood treatment fluid, comprising a blood treatment device 4 arranged in the blood line 3, and the second pressure value can be measured by means of a second sensor 14 mounted at a venous expansion chamber of the blood line, a peristaltic pump 9 being arranged upstream of the blood treatment device 4 and upstream of the venous chamber 16 in order to produce the pulsating thrust of the blood.

The method can comprise a step of further comparison between at least one of the first pressure value and/or the second pressure value with corresponding threshold values and in which the step of emitting the signal indicating a partial or total stenosis is further done on obtaining a predetermined result in the step of further comparison.

The method can comprise a step of emitting a signal representing a partial or total stenosis in the blood line 3, which can be performed on verification of the predetermined result in at least two successive comparisons between the amplitudes calculated in successive temporal instants.

The invention further concerns a software program destined to operate in a control device 12 of blood lines of extracorporeal circuits in medical machines for actuating a method as described herein above.

There follow more detailed descriptions of some specific embodiments of the invention.

In a first embodiment, illustrated in figures from 1 to 7, the invention enables detection of a stenosis located at a first position of the blood line 3. A possible location of the first position is indicated in the figures with reference numeral 100, but the first position might be any position between the arterial expansion chamber and the treatment device 4 in the arterial line 5 or between the pump 9 and the treatment device 4.

Figure 2B:
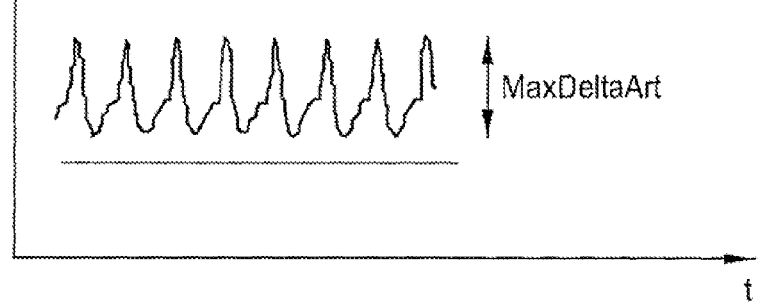

In this first embodiment, the control device 12 receives from the pulse detection sensor 11 of the peristaltic pump 9 a signal corresponding to the passage of the rotor 10, and further receives, from the arterial blood pressure detection sensor 13, a pressure value measured in the arterial expansion chamber, and from the venous blood pressure detection sensor 14 a pressure value measured in the venous expansion chamber. A possible progression of venous and arterial pressure signals provided by the sensors, in normal operating conditions, is illustrated in FIGS. 2a and 2b.

Figure 3:
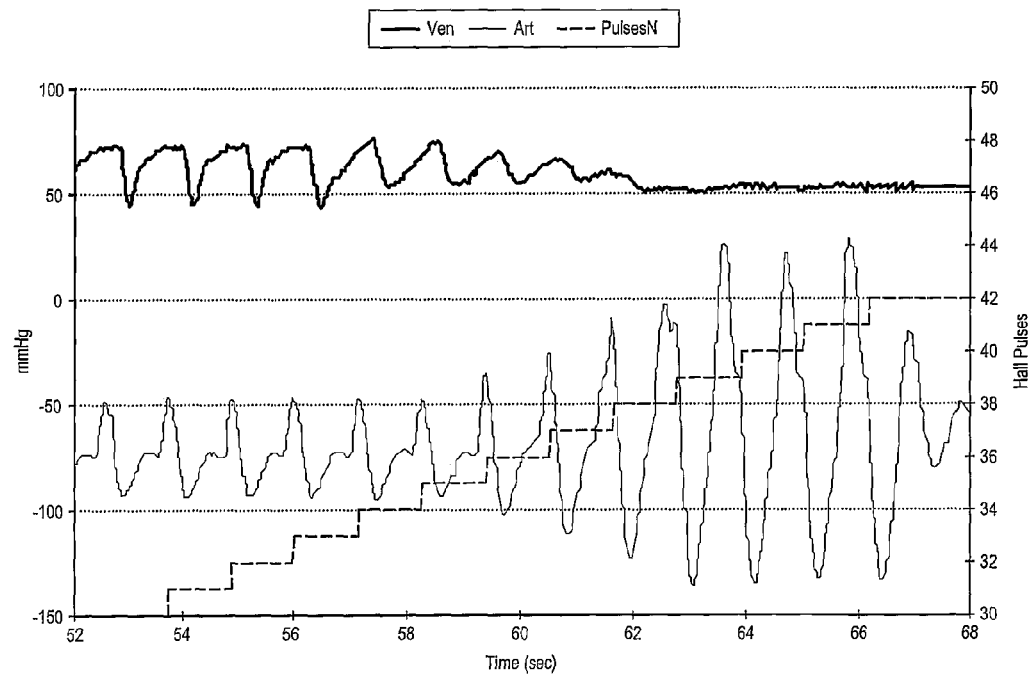
FIG. 3 is a diagram showing a time progression of the arterial pressure and venous pressure measured at respective points of the blood line of FIG. 1, in a situation in which the line functions initially normally and at a determined instant a progressive occlusion occurs, in a first position in the blood line along an arterial line between a blood pump and a treatment device.
Figure 4:
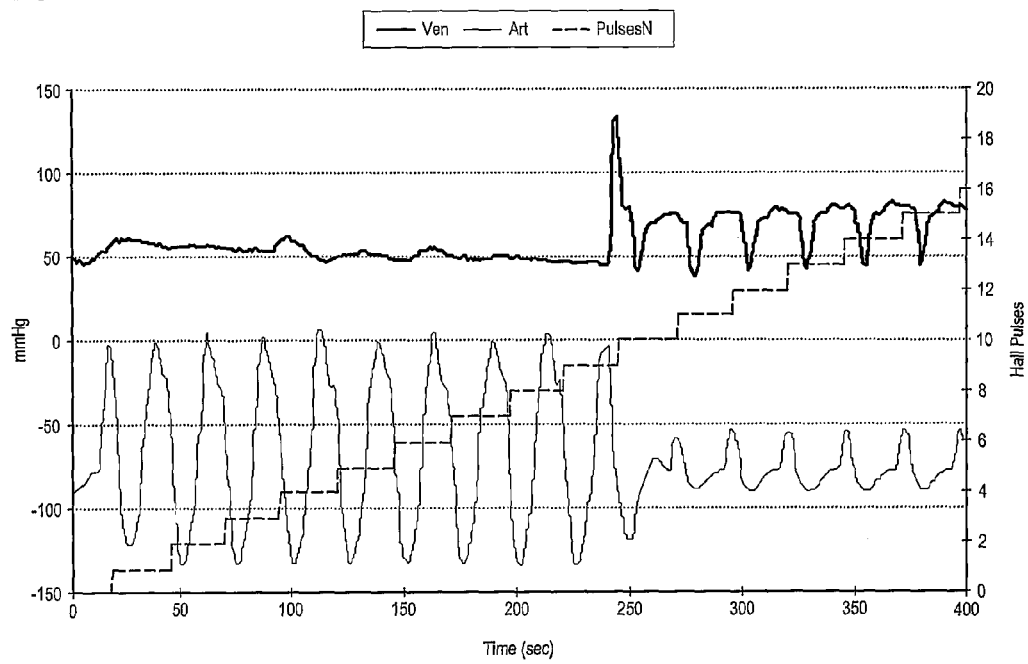
FIG. 4 is a similar diagram to that of FIG. 3, in which in the blood line there is initially present a total occlusion, in the same first position in the blood line between the arterial expansion chamber and the treatment device, and in which the occlusion is subsequently removed.
Figure 5:
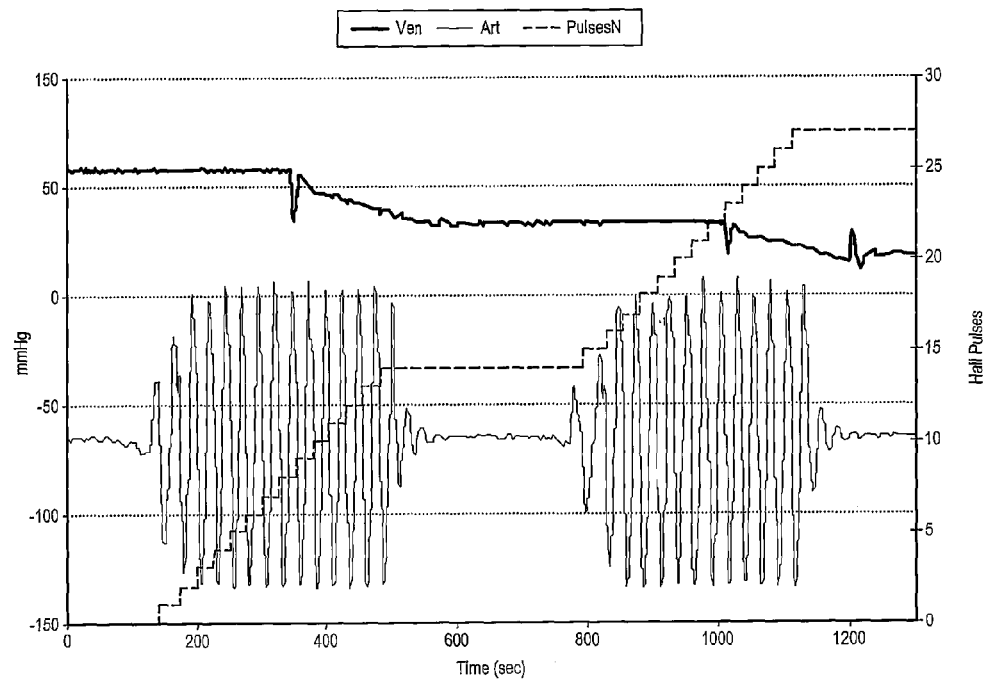
FIG. 5 is a similar diagram to that of FIG. 3, in which an occlusion is present in the blood line in the first position and two alarms are generated without the occlusion being removed.
Figure 7:
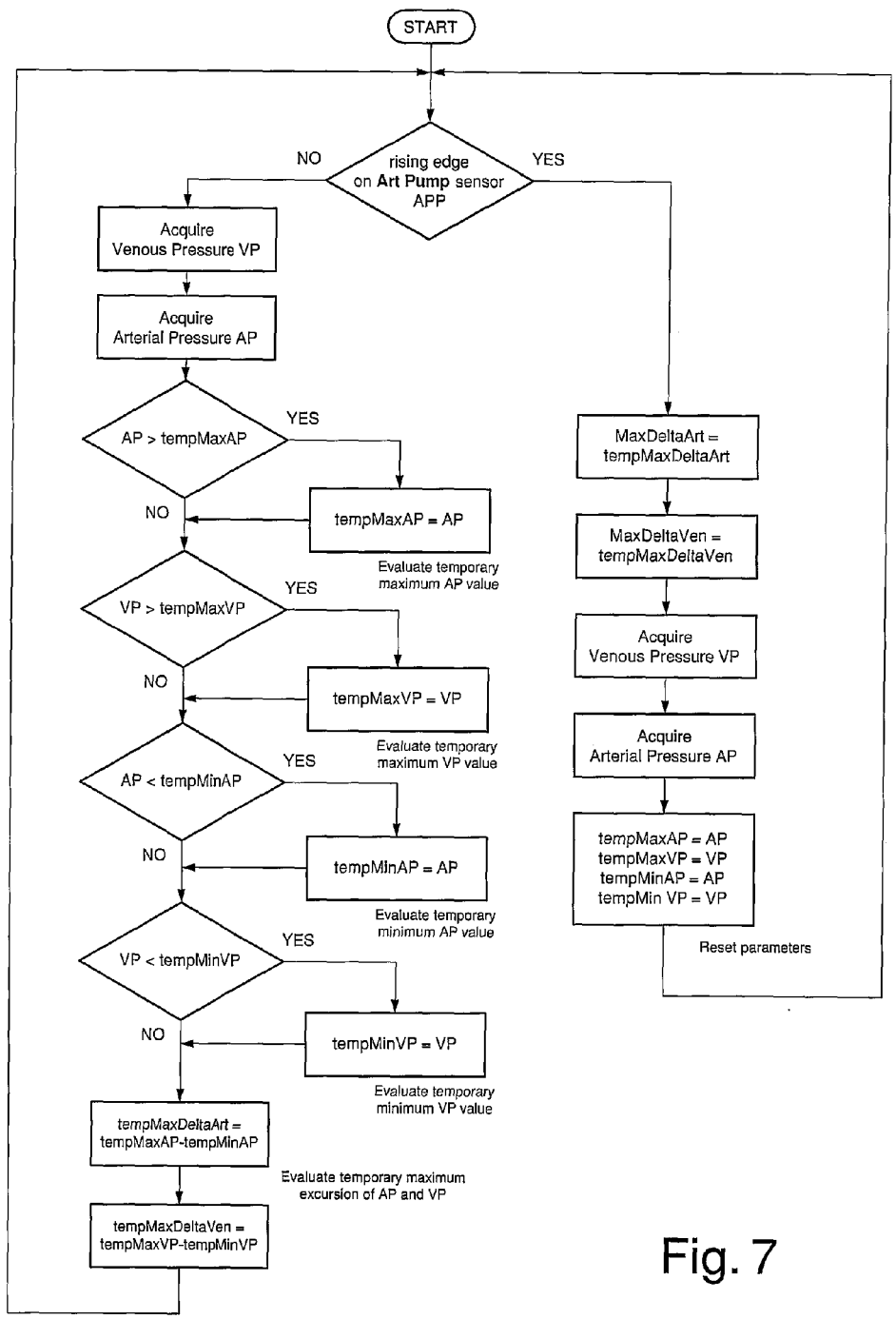
FIG. 7 shows a flow diagram representing some operation performed by a control device of the blood line for monitoring the state of the blood and for the calculation of the amplitude values of FIG. 6 in order to enable a calculation of the relationship between the amplitudes, in accordance with a first embodiment of the invention.

The control device 12, and in particular the processing unit 20, actuate a procedure, illustrated in detail in FIG. 7, for calculating the amplitudes of the arterial pressure signals and the venous pressure signals. In effect, at each instant of sampling of the pressure measurement (and thus for example every 20 ms), the processing unit 20 verifies first if the pulse signal APP is received from the peristaltic pump 9 pulse detection sensor 11, which pulse APP corresponds to the passage of the rotor 10 of the peristaltic pump 9, (which is emitted once for each revolution of the rotor 10 of the pump, and therefore corresponds to a counter of the number of revolutions of the pump 9). The temporal progress of this pulse signal APP is represented in FIGS. 3, 4 and 5 by a stepped line labelled PulsesN. If this pulse signal is not received, the processing unit 20 acquires the two arterial pressure measurements (AP) and venous pressure measurements (VP), and then updates the stored temporary maximum values (tempMaxAP) or temporary minimum values (tempMinAP) of the arterial pressure with the arterial pressure value (AP) just received, in a case in which the value (AP) is respectively greater or smaller than the temporary maximum or temporary minimum previously stored. The same procedure is performed for the temporary maximum (tempMaxVP) and temporary minimum (tempMinVP) for the venous pressure with respect to the just-received value of venous pressure (VP). The processing unit 20 then calculates a temporary value of signal amplitude for the arterial pressure (tempMaxDeltaArt) by subtracting the temporary minimum arterial pressure from the temporary maximum arterial pressure, as possibly updated. A like operation is performed to calculate a temporary amplitude value of the venous pressure signal (tempMaxDeltaVen), by subtracting the temporary minimum venous pressure from the temporary maximum venous pressure, as possibly updated.

This operation is performed cyclically with a frequency that is the same as the sample frequency of the pressure signals. As illustrated in FIG. 7, when the processing unit 20 receives from the peristaltic pump 9 detection sensor 11 a pulse signal corresponding to the passage of the rotor 10 of the peristaltic pump 9, the control unit obtains the maximum amplitude (MaxDeltaArt) of the arterial pressure signal in the latest period of revolution of the rotor 10 of the pump 9 and attributes thereto the presently-stored value (tempMaxDeltaArt), and likewise obtains the maximum amplitude (MaxDeltaVen) of the venous pressure signal in the latest period of revolution of the rotor 10 of the pump 9, attributing thereto the presently-stored value (tempMaxDeltaVen).

Following this operation the control unit obtains a measurement of the arterial (AP) and venous (VP) pressure values and resets the stored temporary parameters, attributing thereto the just-measured values. In accordance with a first embodiment of the invention, the control unit at this point calculates the ratio (Ratio) between the maximum amplitude (MaxDeltaArt) of the arterial pressure signal and the maximum amplitude (MaxDeltaVen) of the venous pressure signal just calculated, obtaining a ratio value as from the following formula:

$$\text{Ratio} = \frac{MaxDeltaArt}{MaxDeltaVen}$$

The ratio value is compared with a ratio threshold value, for example 2.5. If the ratio value (Ratio) is greater than the threshold value for a predetermined number of consecutive readings (i.e. a number of revolutions of the rotor 10), for example for three consecutive readings, the control device 12 emits an alarm signal to indicate the presence of a stenosis in the first position of the blood line 3. In consideration of the fact that in the presence of a stenosis or an occlusion in the circuit the amplitudes of the pulses of the arterial pressure and the venous pressure are considerably different, the ratio between the amplitudes rapidly assumes very high values and it is thus possible very precisely, rapidly and efficiently to detect the presence of stenoses or occlusions.

FIGS. 3 and 4 are diagrams illustrating a progression over time of the arterial pressures (art) and the venous pressures (yen) measured respectively at the arterial expansion chamber and the venous expansion chamber, and the progression of a pulse signal counter (PulsesN) provided by the pulse detection sensor 11 of the peristaltic pump 9.

In the situation illustrated in FIG. 3, the blood line functions normally up to soon after the temporal instant denoted by 60 (Time—sec) in the x-axis, while following that instant a complete occlusion is verified in the blood line, precisely in the arterial line 5 between the pump 9 and the treatment device 4.

Following the occlusion, the two original pulsating signals of arterial and venous pressure are significantly altered, such that the venous pressure pulsating signal is almost totally quashed and becomes irregular, while the arterial pressure pulsating signal is strongly amplified.

In the opposite situation illustrated in FIG. 4, up to soon after the temporal instant denoted by 200 (Time—sec) in the x-axis, there is an occlusion in the arterial line 5 between the pump 9 and the treatment device 4, such that the pulse signal of the venous pressure exhibits a considerably reduced and irregular amplitude, while the pulses of the arterial pressure signal are strongly amplified.

As illustrated in FIG. 4, the occlusion is then removed and the arterial and venous pressure signals normalise, returning to their usual pulsating progression (approximately oscillating), and assuming substantially similar oscillation amplitudes.

Figure 6:
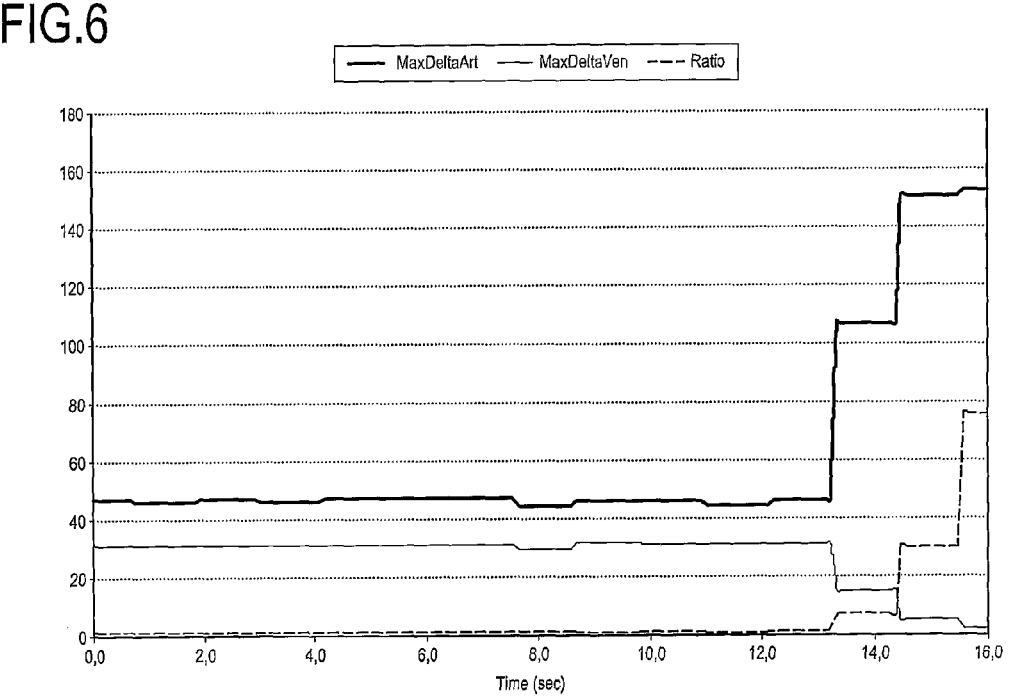
FIG. 6 is a diagram showing a time progression of an amplitude value of the arterial pressure signal and an amplitude value of the venous pressure signal measured in the blood line of FIG. 1 and further shows a time progression of a relationship between the amplitude values, in which an occlusion occurs at a determined instant in the circuit of the first position.

FIG. 5 shows a similar diagram to the one in FIGS. 3 and 4 and relates to a situation in which there is an occlusion in the blood line 3, in the same position as in FIGS. 3 and 4, and several alarms are generated without the occlusion being removed. In particular the system is initially in the shutdown position, with the pump 9 stationary due to an occlusion having been detected, after which the pump 9 is restarted for a few revolutions. The detection of the occlusion, by comparing the amplitudes of the arterial pressure and the venous pressure, causes a new shutdown of the pump 9, commanded by the control device 12. This restarting procedure and new halting of the pump 9 is repeated once more until there is a definitive halting of the pump 9 in order to prevent damage to the circuit or the blood. FIG. 6 is a diagram which shows a progression over time of a maximum amplitude value of the arterial pressure signal (MaxDeltaArt) and of a maximum amplitude value of the venous pressure signal (MaxDeltaVen) measured in the blood line 3 of FIG. 1, and further displays a temporal progression of a ratio between the amplitude values (Ratio). Starting from a temporal instant located between 12 and 14 seconds in the x-axis of the diagram, the arterial and venous amplitude values start changing rapidly, the former growing significantly and the latter dropping almost to zero. The ratio between the two (Ratio) varies even more rapidly and enables the presence of a stenosis or an occlusion in the circuit to be readily detected.

In a second embodiment of the invention, illustrated in figures from 1 to 2 and from 8 to 10, the invention enables detection of a stenosis at a second position in the blood line 3. A possible location of the second position is denoted in the figures by reference numeral 200, but the second position could be anywhere along the venous line 7 between the treatment device 4 and the venous expansion chamber.

It is worthy of note that the second embodiment is actuated, as an example, with the machine in by-pass condition, i.e. with the treatment device 4 hydraulically disconnected from the hydraulic circuit. Generally the by-pass condition is not essential but guarantees only a better reliability during detection.

Consequently, in a case of occlusion in the venous line 7 between the treatment device (dialyser) and the venous expansion chamber, the increase in pressure in the side of the dialyser containing the treatment fluid is greater than the pressure increase in the venous expansion chamber, the control device 12 receives from the peristaltic pump 9 detection sensor 11 a signal corresponding to the passage of the rotor 10, and further receives from the venous blood pressure detection sensor 14 a pressure value measured in the venous expansion chamber, and from a treatment fluid pressure detection sensor 19, mounted in hydraulic circuit connected to the blood treatment device 4 or mounted directly in the treatment device 4.

Figure 8:
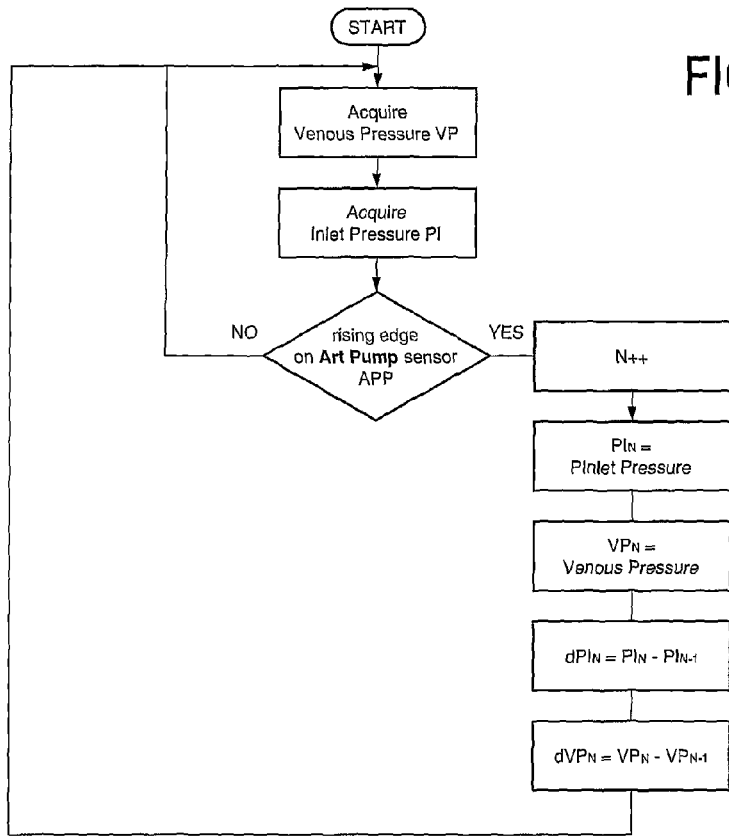
FIG. 8 shows a flow diagram representing some operations performed by a control device of the blood line for monitoring the state of the blood line of FIG. 1 and for the calculation of the differential values of a venous pressure and a pressure of a treatment fluid, in accordance with a second embodiment of the invention.

In particular, the treatment fluid pressure detection sensor 19 is mounted in the illustrated embodiment in the hydraulic circuit at an inlet in the blood treatment device 4. The control device 12, and in particular the processing unit 20, actuate a procedure, illustrated in detail in FIG. 8, for calculating the increased values or differences of the venous pressure signal (VP) and the treatment fluid pressure (PI). In effect, for each sampling instant of the pressure measurement (and thus for example every 20 ms), the processing unit 20 acquires the two values of VP and PI provided by the respective sensors and verifies if the pulse signal corresponding to the passage of the rotor 10 of the peristaltic pump 9 is received by the pulse detection sensor 11 (APP) of the peristaltic pump 9. If this pulse signal is not received, the processing unit 20 waits for the following sampling instant in order to acquire two new VP and PI values. When the signal is received from the pulse detection sensor 11, a counter of the processing unit 20 activates, attributing to a variable $PI_N$ the treatment fluid pressure value in the current instant N, and attributing to a variable $VP_N$ the venous pressure in the current instant N. The processing unit 20 then calculates an increase value or a pressure differential of the treatment fluid $dPI_N$ given by the difference between the treatment fluid pressure value at the current instant N and the value of this pressure in the immediately preceding instant N−1. Likewise an increase value or venous pressure differential $dVP_N$ is calculated, given by the difference between the venous pressure value at the current instant N and the value of this pressure in the immediately-preceding instant N−1.

At this point the processing unit 20 calculates the difference between the increase value of the treatment fluid pressure $dPI_N$ and the increase value of the venous pressure $dVP_N$ and compares the difference value thus obtained with a difference threshold. If the difference value exceeds the threshold, and further if the current pressure value $PI_N$ exceeds a relative maximum venous pressure threshold, the control device 12 emits an alarm and/or halts the pump 9, possibly actuating a suitable shutdown procedure.

In detail, the processing unit 20 uses the following verification formula:

$$(dPI_N - dVP_N > \text{MaxThreshold}) \text{ AND}$$
$$(PI_N > \text{MaxPIpress})$$

Figure 9:
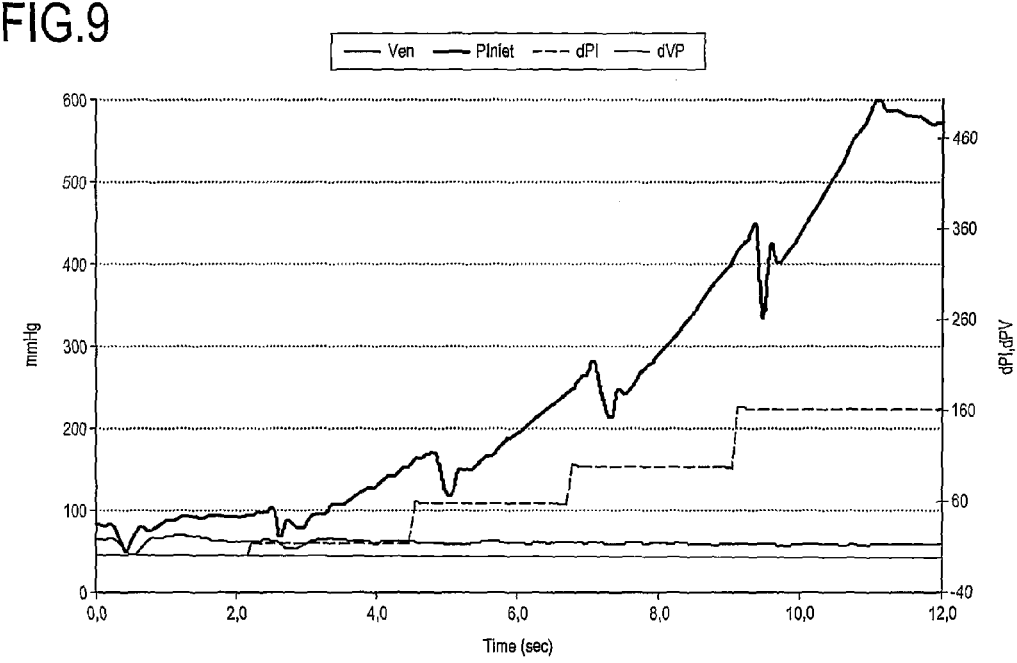
FIG. 9 is a diagram showing a time progression of venous pressure levels, treatment fluid pressure and respective different venous pressure values and a treatment pressure value at two successive temporal instants, in the presence of an occlusion in a second position of the blood line of FIG. 1, along the venous line, between a treatment device and a venous expansion chamber.

FIG. 9 is a diagram representing a temporal progression respectively of the venous pressure value (VP or Venous Press), the treatment fluid pressure value (PI or Pinlet) measured in the blood line 3 of FIG. 1, the differential increase value of the venous pressure (dVP) and the differential increase value of the treatment fluid pressure value (sPI), all in the presence of an occlusion between the treatment device 4 and the venous expansion chamber. As illustrated in FIG. 9, in the presence of an occlusion in this position there is a progressive drop in the venous pressure up to becoming almost constant, while there is a pulse having a contemporaneous significant increase of the pressure value of the treatment fluid. Consequently the differential increase value of the venous pressure value (dVP) remains almost zero between a cycle of the pump 9 and the following, while the differential increase value of the treatment fluid pressure (sPI) increases at each cycle. The above-cited formula thus enables timely detection of the presence of a stenosis or occlusions in the circuit.

Figure 10:
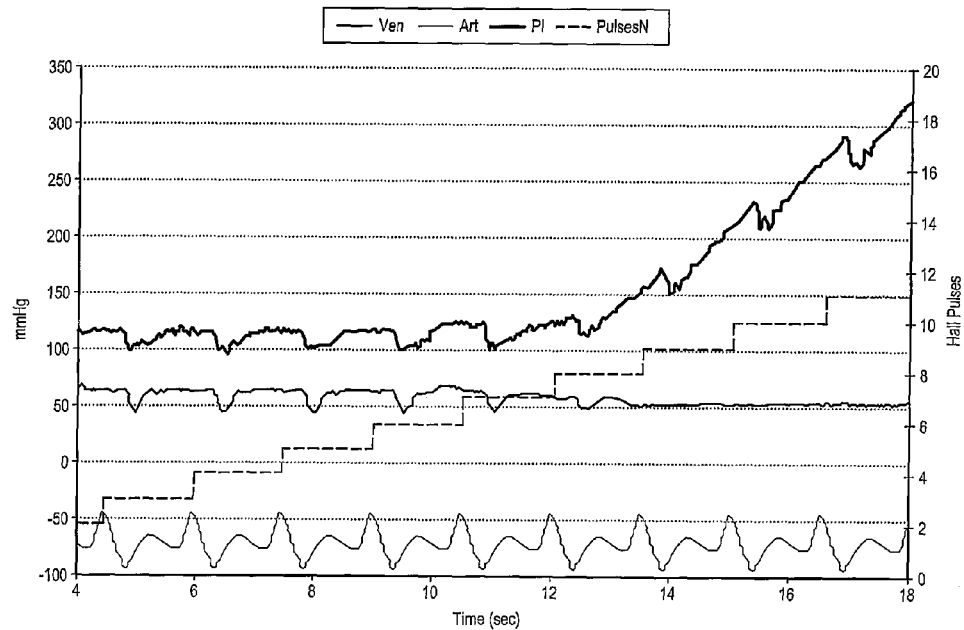
FIG. 10 is a similar diagram to that of FIG. 3, wherein a time progress is shown of the arterial pressure and the venous pressure, and of the pressure of a treatment fluid, measured at respective points in the blood line of FIG. 1, in a situation in which the line functions initially normally and at a determined instant a progressive occlusion occurs, in a second position in the blood line along a venous line between the treatment device and the venous expansion chamber.

In a variant of the second embodiment, similarly to what is described above the invention can enable detection of a stenosis located at a second position of the blood fine 3, between the treatment device 4 and the venous expansion chamber, in the venous line 7, also by means of the above-illustrated procedure with respect to the first embodiment. As illustrated in the diagram of FIG. 10, in relation to the blood line of FIG. 1 (by way of example), in the presence of an occlusion in the second position, there is a relevant drop in the pulse amplitude of the venous pressure, while the pulse of the treatment fluid pressure stays at a significant level, while at the same time the absolute value of the pressure of the treatment fluid increases. Thus, also applying the calculation formulae illustrated for the first embodiment to the amplitudes of the treatment fluid pressure (instead of to the arterial pressure) and the venous pressure, it is possible to detect likewise the presence of a stenosis or occlusion at the second position of the blood line.

In a third embodiment of the invention, illustrated in FIGS. 1, 2, 8 and 11, the invention enables detection of a stenosis at a third position in the blood line 3.

A possible location of the third position is denoted in the figures with reference numeral 300, but the first position could be any position along the venous line 7 between the venous expansion chamber and the venous access 8 to the patient, i.e. along the venous line downstream of the venous expansion chamber. This third embodiment too is actuated with the machine in by-pass condition, i.e. with the treatment device 4 hydraulically disconnected from the hydraulic circuit. Also in this case, as in the previous one, the by-pass is not essential but makes the reading more reliable.

In this embodiment, the control device also receives, from the peristaltic pump 9 pulse detection sensor 11, a signal corresponding to the passage of the rotor 10. The control device 12 further receives, from the venous blood pressure detection sensor 14, and from a treatment fluid pressure detection sensor 19, mounted in the hydraulic circuit connected to the blood treatment device 4 or mounted directly in the treatment device 4, a treatment fluid pressure value. In particular, the treatment fluid pressure detection sensor 19 is mounted, in the illustrated embodiment, in the hydraulic circuit at an inlet of the blood treatment device 4.

The control device 12, and in particular the processing unit 20, actuate the same procedure as described above and illustrated in detail in FIG. 8, for the calculation of the increase or differential values of the venous pressure signals (PN) and the treatment fluid pressure (PI) signals. In this case, however, the processing unit 20 no longer calculates the difference between the increase value of the treatment fluid pressure $dPI_N$ and the increase value of the venous pressure $dVP_N$. The processing unit 20 in this case compares the increase value of the venous pressure $dVP_N$ and the increase value of the treatment fluid pressure $dPI_N$ with relative thresholds, and further compares the current venous pressure values and the treatment fluid values with further respective thresholds. If all four of the indicated thresholds are exceeded, the control device 12 emits an alarm and/or halts functioning of the pump 9, possibly actuating a suitable shutdown procedure. In detail, the processing unit 20 uses the following verification formulae.

$$(dPI_N > \text{Max}dPI) \text{ AND}$$

$$(dVP_N > \text{Max}dVP) \text{ AND}$$

$$(PI_N > \text{MaxPIpress}) \text{ AND}$$

$$(VP_N > \text{MaxVPpress})$$

Figure 11:
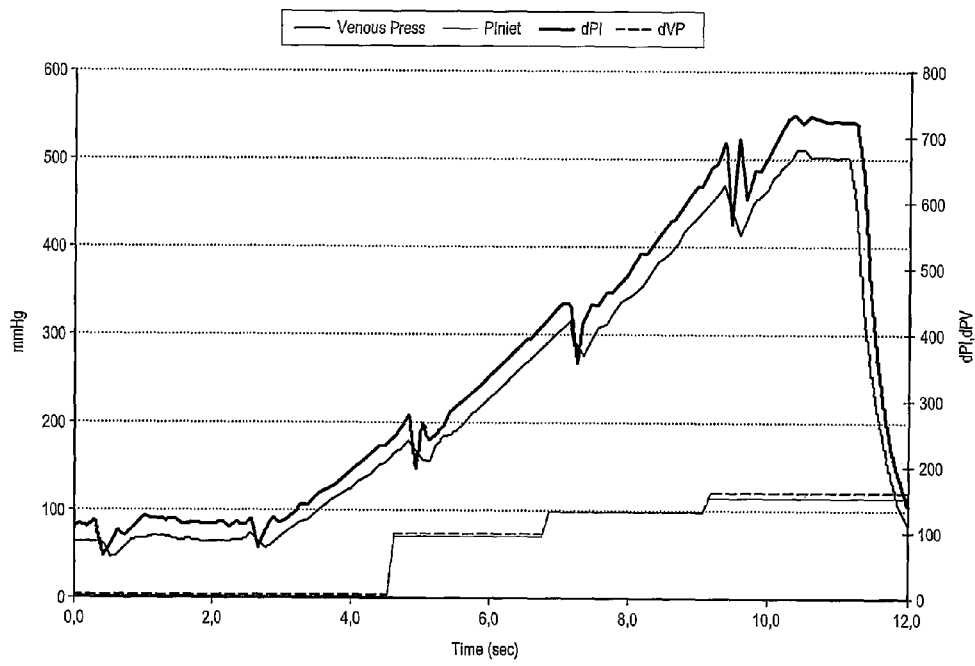
FIG. 11 is a similar diagram to that of FIG. 9, in the presence of an occlusion in a third position in the blood line of FIG. 1, along the venous line and downstream of a venous expansion chamber.

FIG. 11 is a diagram showing the temporal progression respectively of the venous pressure value (VP or Venous Press), the treatment fluid pressure vale (PI or Pinlet) measured in the blood line 3 of FIG. 1, of the difference increase of the venous pressure (dVP) and the increase of the treatment fluid pressure value (dPI), in the presence of an occlusion along the venous line 7 downstream of the venous expansion chamber.

As illustrated in FIG. 11, in the presence of an occlusion in this position there are two pulsating and growing progressions of the venous pressure value and the treatment fluid pressure value. Also the increase difference in the venous pressure value (dVP) and increase difference value of the treatment fluid pressure value (dPI) grow at each cycle. In this case too the indicated formula enables prompt detection of the presence of a stenosis or occlusions in the circuit.

As mentioned herein above, the invention is applicable, in a substantially similar way, also in a circuit for hemodiafiltration (HDF) such as the one illustrated in FIG. 12, to detect stenoses at the same positions as indicated above with like methods. The circuit, in itself of known type and therefore not illustrated in detail, can comprise, apart from the already-cited elements with respect to the hemodialysis circuit (HD) of FIG. 1, a pre-infusion line 21 for a fluid to be added to the blood and/or a post-infusion line 22 for the fluid. The pre-infusion line 21 enters the blood line 3 at the arterial line 5 (upstream of the treatment device 4) while the post-infusion line 22 enters at the venous line 7 (downstream of the treatment device 4). A pre-filtration chamber 23 is located at least in the pre-infusion line 21, with a relative pressure sensor 24 of the fluid to be added to the blood. The pre-infusion line 21 and the post-infusion line 22 can originate from a single infusion line 25 which divides into two branches defining the two lines of pre- and post-infusion 21, 22, which are selectable by means of appropriate selection valves 26, 27. The infusion line 25 is further provided with at least a filter 28, with at least an infusion pump 29 and a source 30 of the fluid to be added.

Figure 12:
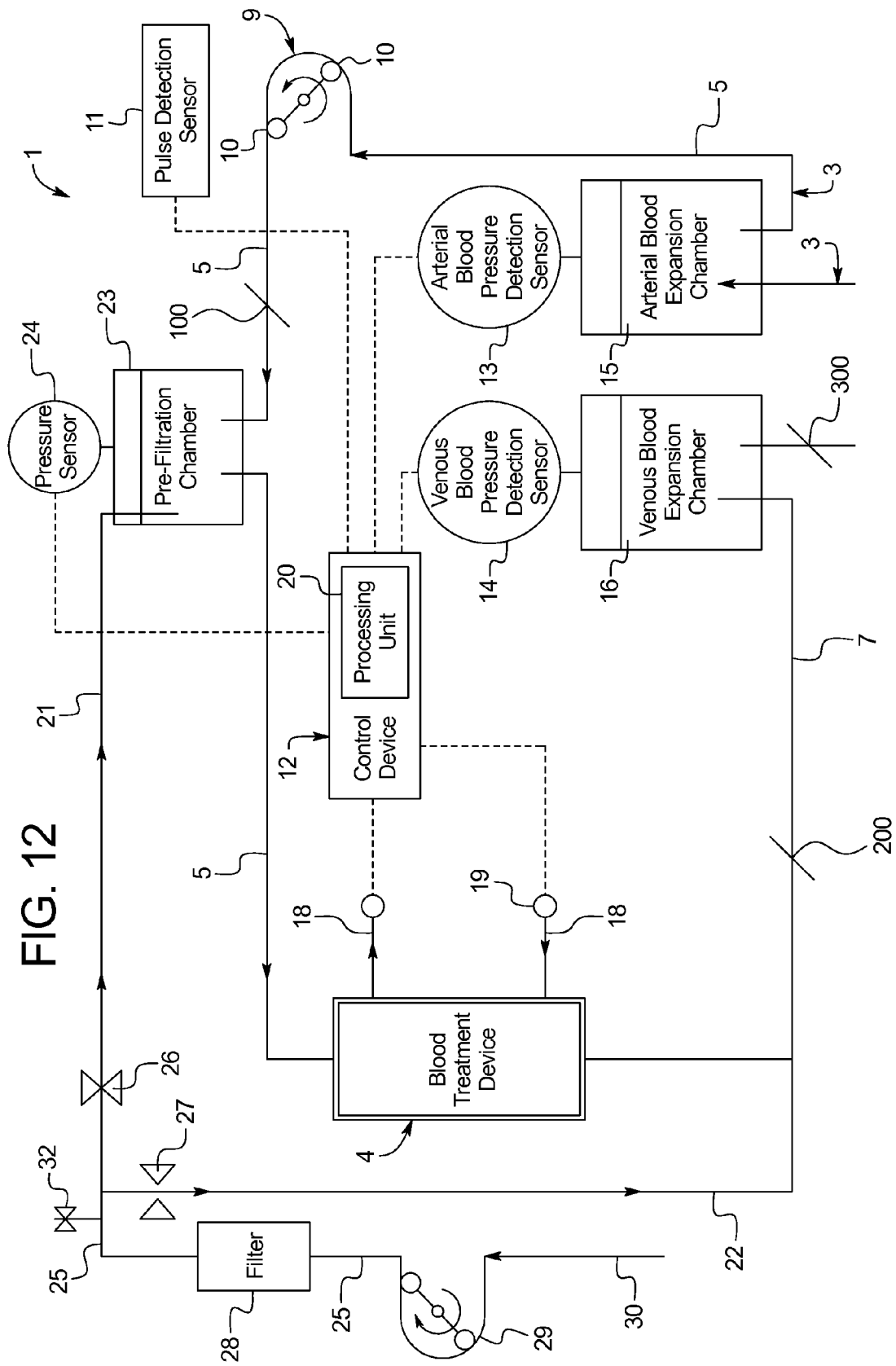
FIG. 12 is a schematic view, in accordance with further embodiments of the present invention, of a blood line being part of an apparatus for extracorporeal blood treatment by means of a hemo(dia)filtration (HDF)
Figure 13:
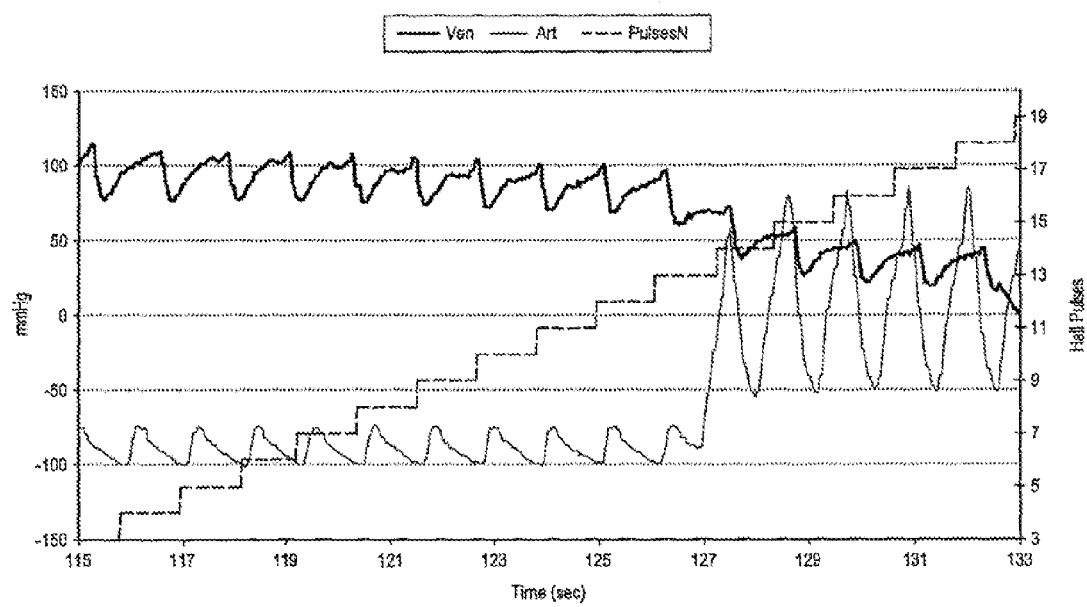
FIG. 13 is a similar diagram to that of FIG. 3, relating to the hemo(dia)filtration circuit (HDF) of FIG. 12, and shows a time progression of the arterial pressure and the venous pressure measured at respective points of the blood line of FIG. 12, in a situation in which the line initially functions normally and at a determined instant a progressive occlusion occurs, in a first position in the blood line along an arterial line between a blood pump and a treatment device.

FIG. 13 shows the progress of the arterial and venous pressures in the blood line of FIG. 12, in which the blood line 3 functions normally up to a certain instant and then is subjected to a partial stenosis in a first position of the blood line, between the pump and the treatment device 4. In this case too the pulse amplitude of the arterial pressure grows significantly and become much greater than the pulse amplitude of the venous pressure, and therefore, by means of the procedure illustrated for the first embodiment, it is possible to detect the presence of the stenosis, even when partial. The methods of the second and the third embodiments are also similarly applicable to the circuit of FIG. 12.

Figure 14:
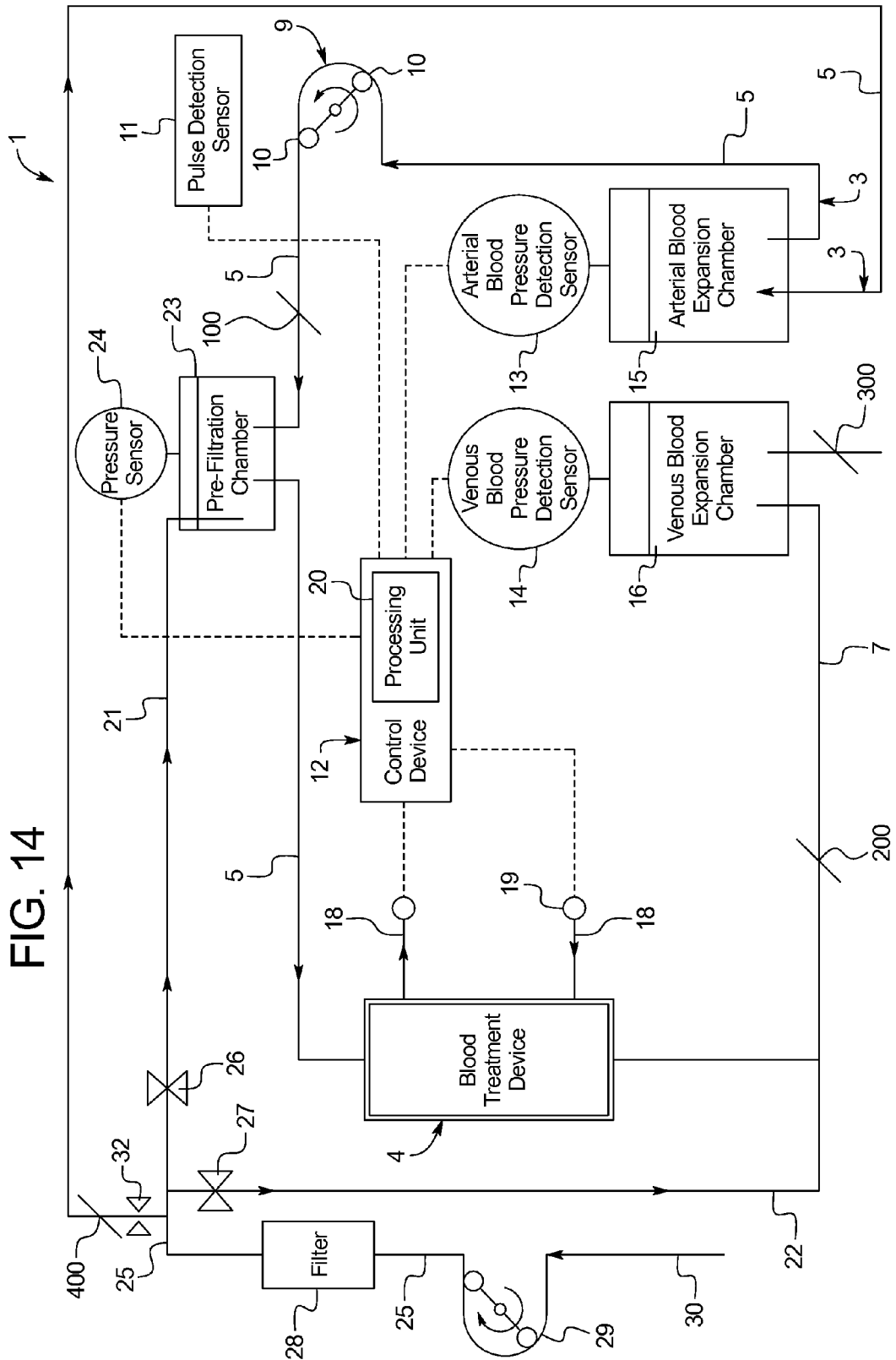
FIG. 14 shows the blood line being part of the apparatus for extracorporeal blood treatment by means of a hemo(dia)filtration treatment of FIG. 12, in which the apparatus is configured to perform a rinseback process (sending the blood back to the patient at the end of the treatment)
Figure 15:
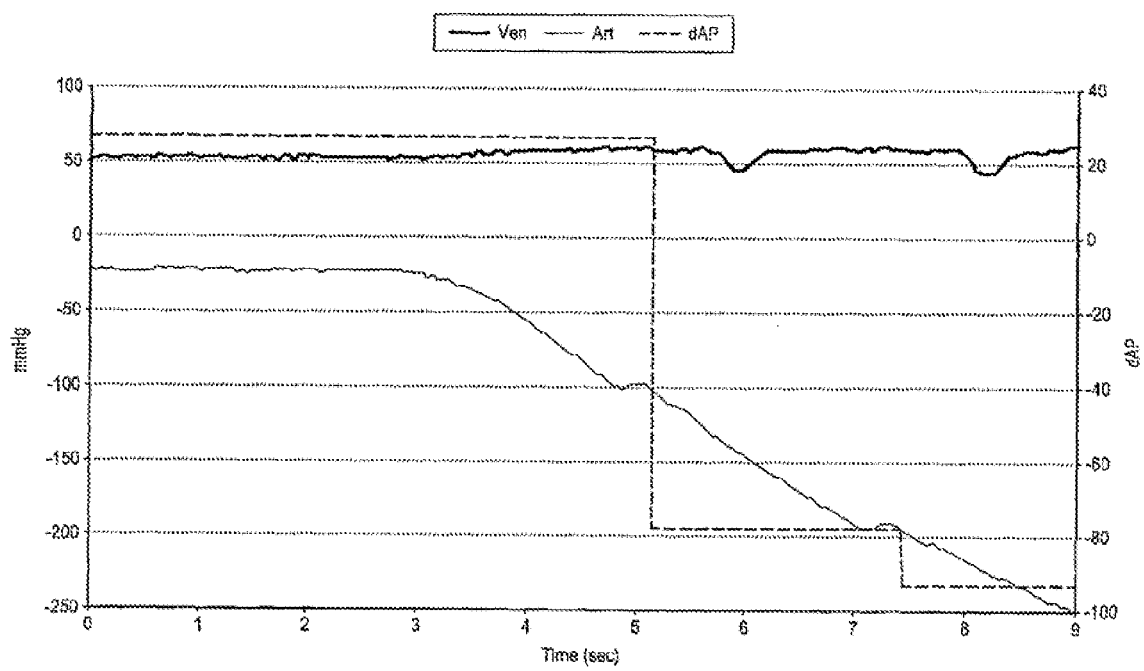
FIG. 15 is a diagram illustrating a progress of the arterial values, the venous values and a difference in the arterial pressure in the presence of an occlusion in a fourth position in the blood line of FIG. 14, in accordance with the fourth preferred embodiment of the invention.
Figure 16:
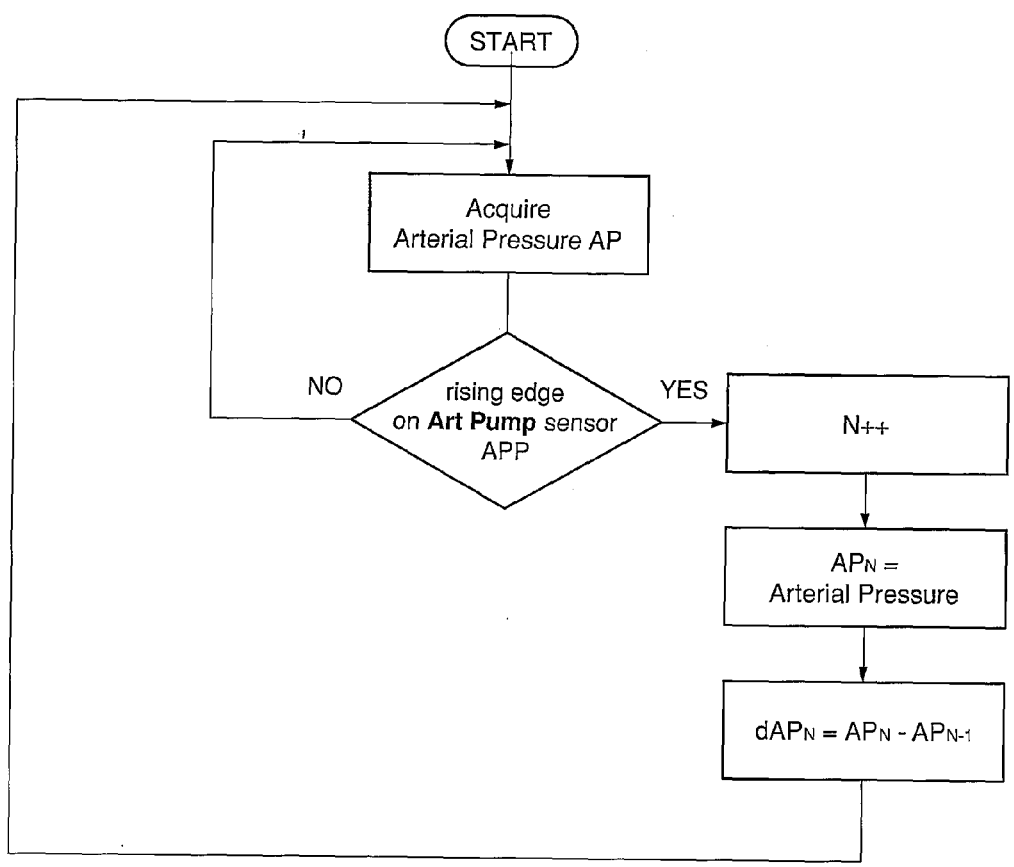
FIG. 16 shows a flow diagram showing some operations performed by a control device of the blood line for monitoring the state of the blood line of FIG. 14 and for the calculation of different values of an arterial pressure, in accordance with a fourth embodiment of the invention.

As illustrated in FIGS. 14-16, and according to a fourth embodiment, the invention enables detection of a stenosis at a fourth position of the blood line 3. A possible location of the fourth position is indicated in the figures with reference numeral 400, but the first position might be any position along the arterial line 5 and upstream of the arterial expansion chamber 15 of the blood.

FIG. 14 illustrates a hemodiafiltration (HDF) circuit, similar to the one illustrated in FIG. 12 but configured for performing a rinseback process, i.e. sending the blood back to the patient at the end of the treatment. In this configuration the infusion line is provided with a further connection line 31 which connects the infusion line 25 downstream of the filter 28 with the arterial line 5 upstream of the arterial expansion chamber 15, while the selection valves 26, 27 of the pre- and post-infusion lines 21 and 22 are closed. A further selection valve 32, which in the preceding configuration was closed, must in this case be open. The fourth position can be located along the connection line 31. In the fourth embodiment, the control device 12 receives from the peristaltic pump 9 pulse detection sensor 11 a signal corresponding to the passage of the rotor 10, and further receives from the arterial blood pressure detection sensor 13 the pressure value measured in the arterial expansion chamber 15.

The control device 12, and in particular the processing unit 20, actuate a procedure, illustrated in detail in FIG. 16, for calculating the increase or difference value of the arterial pressure signal (AP). At each sampling instant of the pressure measurement (and thus for example every 20 ms), the processing unit 20 acquires the AP value and if the pulse signal corresponding to the passage of the rotor 10 of the peristaltic pump 9 is not received by the pulse detection sensor 11 (APP) of the peristaltic pump 9, the next sampling instant is passed on to. If the signal is received, a counter of the processing unit 20 is added to, attributing to a variable $AP_N$ the arterial pressure value in the current instant N and then calculating an increase or differential value of arterial pressure $dAP_N$ given by the difference between the arterial pressure value in the current instant N and the value of the pressure in the immediately preceding instant N−1. At his point the processing unit 20 compares the increase value, or decrease value, of the arterial pressure $dAP_N$ with a minimum decrease threshold. If the decrease value $dAP_N$ is lower than the threshold decrease value the control device 12 emits an alarm and/or halts the pump 9, possibly actuating a suitable shutdown procedure, in order to prevent damage to the part of the system and the blood remaining in the blood line 3. In detail, the processing unit 20 uses the following verification formula:

$$(dAP_N < Min\,dAP)$$

The procedure performed by the processing unit is illustrated in detail in FIG. 16. FIG. 15 shows a diagram illustrating the progression of the arterial pressure, the venous pressure and the dAP parameter (arterial pressure differential) in the presence of an occlusion in the circuit of the fourth position, which occlusion occurs at more or less 3 seconds on the x-axis.

The fourth embodiment is particularly useful for preventing an operator, after having connected the filter device to perform the rinseback procedure on the circuit, from forgetting to remove the clamp at the fourth position (for example by not opening the selection valve 32) and setting off the procedure, causing in many cases the breakage of some part of the circuit. Worthy of note is the fact that in the prior art a similar situation would not be detected as the arterial pressure value would remain in any case over the normal alarm thresholds.

The invention provides important advantages and obviates some of the drawbacks in the prior art. In particular the described invention enables attaining one or more of the aims previously defined. A final point is that the invention is further applicable to different circuits from the ones illustrated.

The invention claimed is:

1. A method for detecting a presence of a partial or total occlusion in a blood line in a circuit for extracorporeal blood treatment, comprising:
    acquiring at least a first pressure value from a first sensor mounted at a first point of the circuit for extracorporeal blood treatment, said circuit a blood line in which the blood is subjected to a pulsating thrust and a blood treatment device arranged in the blood line, wherein a peristaltic pump is arranged upstream of the blood treatment device and upstream of a venous chamber of the blood line in order to produce the pulsating thrust of the blood;
    acquiring at least a second pressure value from a second sensor mounted at a second point, distinct from the first point, of the blood line of the circuit for extracorporeal blood treatment, and
    relating at least a first value, related to the first pressure value, and at least a second value, related to the second pressure value, with at least a threshold value, to obtain a datum representing a state of partial or total occlusion in the blood line in the circuit for extracorporeal blood treatment,
    wherein the first pressure value is measured by a first sensor mounted in a hydraulic circuit for a blood treatment fluid and wherein the second pressure value is measured by a second sensor mounted at the venous chamber of the blood line.

2. The method of claim 1, further comprising emitting a signal representing the state of the blood line when the datum conforms to a predetermined alarm value.

3. The method of claim 1, further comprising emitting an alarm signal and/or arresting the functioning of a pump in the circuit, when the datum indicate presence of a condition of partial or total occlusion in the blood line.

4. The method of claim 2, wherein the step of emitting a representative signal of a partial or total occlusion in the blood line is carried out on verification of a predetermined result in at least two successive comparisons between pressure values calculated in successive temporal intervals.

5. The method of claim 2, wherein the step of emitting a signal representing the state of the blood line is performed when obtaining a predetermined value for the datum for a predetermined number of consecutive times at a predetermined number of distinct and successive temporal instants.

6. The method of claim 1, further comprising acquiring a plurality of the first pressure values and a plurality of the second pressure values, the first and second pressure values being sampled and detected at a plurality of corresponding successive temporal instants that are distanced from one another by a predetermined time interval.

7. The method of claim 6, in which the time interval corresponds to a step of the relative pressure impulse signals.

8. The method of claim 1, wherein the step of relating at least a first value related to the first pressure value and at least a second value related to the second pressure value with at least a threshold value in order to obtain a datum representing a state of the blood line is performed only at a specific angular position of a rotor of a peristaltic pump mounted in the circuit.

9. The method of claim 8, further comprising comparing at least one of the first pressure value and/or the second pressure value with corresponding threshold values, and in which the step of emitting the signal representing a partial or total occlusion is carried out in response to a predetermined result of the step of further comparison.

10. The method of claim 1, wherein the first value and the second value are respectively related to corresponding differences between two first pressure values measured by the first sensor in two successive and distinct temporal instants and between two second pressure values measured by the second sensor in the two successive and distinct temporal instants.

11. The method of claim 1, comprising a step of performing at least a subtraction between the first value and the second value and comparing a result of the subtraction with a threshold value in order to obtain the datum representing a state of the blood line.

12. The method of claim 1, further comprising individually comparing respectively the first value and the second value with respective threshold values to obtain the datum representing a state of the blood line.

13. The method of claim 1, further comprising calculating at least two first values related to the first pressure value and/or at least two second values related to the second pressure value, and steps of relating the first two values with respective threshold values and/or the two second values with respective threshold values in order to obtain the datum representing a state of the blood line.

14. The method of claim 1, wherein a first pressure value and a second pressure value are read at a same moment at two distinct points in the circuit.

15. The method of claim 1, wherein the signal representing a partial or total occlusion in the blood line is emitted in a case in which the change in the first pressure value is lower than a predetermined decrease threshold value.

16. A method to detect partial or total occlusions of a blood line in an extracorporeal blood treatment apparatus, the method comprising:
determining a first pressure pulsation value in the blood line at a withdrawal portion of the blood line receiving arterial blood withdrawn from a patient, wherein the arterial blood is subject to a pulsating thrust due to a beating heart of the patient and the pressure pulsation value indicates a pressure variation due to the pulsating thrust, wherein the determination of the first pressure pulsation value includes determining a difference between at least two pressure measurements made during successive temporal instants;
determining a second pressure pulsation value in the blood line at an infusion portion of the blood line returning venous blood to the patient, wherein the second pressure pulsation value is sensed and acquired within a certain temporal interval during which the first pressure pulsation value is sensed and acquired;
comparing the first pressure pulsation value to the second pressure pulsation value; and
emitting a signal representing a partial or total occlusion in the blood line in response to the comparison.

17. The method of claim 16 wherein the determination of the first pressure pulsation value includes acquiring successive first pressure values from a first pressure sensor monitoring the withdrawal portion of the blood line, and comparing the acquired successive first pressure values to determine the first pressure pulsation value.

18. An apparatus for extracorporeal blood treatment comprising:
at least a circuit for extracorporeal blood treatment, the circuit for extracorporeal blood treatment including at least a blood treatment device and a blood line, the blood line including an arterial line destined to carry the blood from an arterial access of a patient to the blood treatment device and at least a venous line destined to carry the blood from the blood treatment device to a venous access of a patient;
at least a peristaltic pump for the blood mounted in the extracorporeal circuit to push the blood at a thrust pressure having a pulsating progression over time;
at least a detection sensor of arterial blood pressure mounted at a first point of the circuit for extracorporeal blood treatment upstream of the pump;
at least a detection sensor of venous blood pressure mounted at a second point of the circuit for extracorporeal blood treatment downstream of the pump;
a hydraulic circuit for a treatment fluid of the blood, operatively connected to the blood treatment device,
at least a pressure detection sensor of the treatment fluid mounted in the hydraulic circuit; and
a control device operatively connected at least to the detection sensor of arterial pressure and/or to the detection sensor of venous pressure and/or to the pressure detection sensor of the treatment fluid, the control device including a processing unit configured to execute a procedure stored in a non-transitory memory of the control device to cause the apparatus for extracorporeal blood treatment to:
determine a first pressure pulsation value at the arterial line receiving arterial blood withdrawn from a patient, wherein the arterial blood is subject to the pulsating thrust due to the peristaltic pump and the pressure pulsation value indicates a pressure variation due to the pulsating thrust;
determine a second pressure pulsation value at the venous line returning venous blood to the patient, wherein the second pressure pulsation value is sensed and acquired within a certain temporal interval during which the first pressure pulsation value is sensed and acquired;
compare the first pressure pulsation value to the second pressure pulsation value, and emit a signal representing a partial or total occlusion in the blood line of the circuit for extracorporeal blood treatment in response to the comparison,
wherein, using the corresponding pressure signals acquired by the sensors, the processing unit is further configured to execute a procedure stored in the non-transitory memory of the control device to cause the apparatus for extracorporeal blood treatment to:
relate at least a first value, related to the first pressure pulsation value, and at least a second value, related to the second pressure pulsation value, with at least a threshold value, to obtain a datum representing a state of partial or total occlusion in the blood line of the extracorporeal blood treatment circuit.

19. The apparatus of claim 18, wherein an arterial pressure detecting sensor of the blood is mounted in an arterial blood expansion chamber and a venous pressure detecting sensor is mounted in a venous blood expansion chamber.

20. The apparatus of claim 1, wherein said first value is a pressure differential value between a first pressure value and a second pressure value measured by the first sensor in the hydraulic circuit in successive temporal intervals and said second value is a pressure differential value between a first pressure value and a second pressure value measured by the second sensor at the venous expansion chamber in said successive temporal intervals.

21. The apparatus of claim 20, wherein the step of relating the first value and the second value with the threshold value includes the step of calculating the difference between the first and the second value and of comparing the difference with said threshold value.

22. The apparatus of claim 21, further including the step of comparing the first or the second pressure value measured by the first sensor in the hydraulic circuit with a maximum threshold value.

23. The apparatus of claim 22, wherein the datum representing the a state of partial or total occlusion in the blood line of the circuit for extracorporeal blood treatment depends on both the step of comparing the difference between the first and the second value with said threshold value and the step of comparing the first or the second pressure value with said maximum threshold value.

24. The apparatus of claim 23, wherein the presence of a partial or total occlusion in the blood line of the circuit for extracorporeal blood treatment is determined if the difference between the first and the second value exceeds said threshold value and the first or the second pressure value exceeds said maximum threshold value.

25. The apparatus of claim 1, wherein said first value is a pressure differential value between a first pressure value and a second pressure value measured by the first sensor in the hydraulic circuit in successive temporal intervals, the step of relating the first value and the second value with the threshold value includes the step of comparing said first value with a maximum first value threshold.

26. The apparatus of claim 1, wherein said second value is a pressure differential value between a first pressure value and a second pressure value measured by the second sensor at the venous expansion chamber in said successive temporal intervals, the step of relating the first value and the second value with the threshold value includes the step of comparing said second value with a maximum second value threshold.

27. The apparatus of claim 1, wherein further includes the step of comparing the first or the second pressure value measured by the first sensor in the hydraulic circuit with a maximum hydraulic threshold value.

28. The apparatus of claim 1, wherein further includes the step of comparing the first or the second pressure value measured by the second sensor at the venous expansion chamber with a maximum venous threshold value.

29. The apparatus of claim 1, wherein the datum representing the state of partial or total occlusion in the blood line of the circuit for extracorporeal blood treatment depends on one or more of the steps of:
comparing said first value with a maximum first value threshold;
comparing said second value with a maximum second value threshold;
comparing the first or the second pressure value measured by the first sensor with a maximum hydraulic threshold value; and
comparing the first or the second pressure value measured by the second sensor with a maximum venous threshold value.

30. The apparatus of claim 29, wherein the datum representing the state of partial or total occlusion in the blood line of the circuit for extracorporeal blood treatment is determined if:
said first value exceeds the maximum first value threshold;
said second value exceeds the maximum second value threshold;
the first or the second pressure value measured by the first sensor exceeds the maximum hydraulic threshold value; and
the first or the second pressure value measured by the second sensor exceeds the maximum venous threshold value.

31. The apparatus of claim 1, wherein the blood line includes an arterial line destined to carry the blood from an arterial access of a patient to the blood treatment device and at least a venous line destined to carry the blood from the blood treatment device to a venous access of a patient, the presence of the partial or total occlusion in the blood line of the circuit for extracorporeal blood treatment being detected along the venous line.

32. The apparatus of claim 31, wherein the presence of the partial or total occlusion in the blood line of the circuit for extracorporeal blood treatment is detected along the venous line between the treatment device and the venous expansion chamber.

33. The apparatus of claim 31, wherein the presence of the partial or total occlusion in the blood line of the circuit for extracorporeal blood treatment is detected along the venous line between the venous expansion chamber and the venous access.

34. The apparatus of claim 18, wherein said first pressure pulsation value is an amplitude of the arterial blood pressure and said second pressure pulsation value is an amplitude of the venous blood pressure.

35. The apparatus of claim 18, wherein the step of comparing the first pressure pulsation value to the second pressure pulsation value includes the step of obtaining a ratio between the first pressure pulsation value and the second pressure pulsation value and comparing the ratio with the threshold value.

36. The apparatus of claim 35, wherein the step of obtaining the ratio is performed a plurality of times during treatment to obtain a plurality of corresponding ratios, said plurality of ratios being compared with the threshold value and the partial or total occlusion in the blood line of the circuit for extracorporeal blood treatment being detected as a function of a plurality of comparisons between the ratios and the threshold value.

37. The apparatus of claim 35, wherein the partial or total occlusion in the blood line of the circuit for extracorporeal blood treatment is detected if the ratio exceeds the threshold value.

38. The apparatus of claim 35, wherein the partial or total occlusion in the blood line of the circuit for extracorporeal blood treatment circuit is detected if the ratio exceeds the threshold value a plurality of consecutive times.

39. The apparatus of claim 18, wherein the presence of the partial or total occlusion in the blood line of the circuit for the extracorporeal blood treatment is detected along the arterial line.

40. The apparatus of claim 18, wherein the extracorporeal blood treatment circuit further includes an arterial blood expansion chamber, and wherein the presence of the partial or total occlusion in the blood line of the circuit for extracorporeal blood treatment is detected along the arterial line between the arterial expansion chamber and the blood treatment device.

41. The apparatus of claim 40, wherein the presence of the partial or total occlusion in the blood line of the extracorporeal blood treatment circuit is detected along the arterial line between the peristaltic pump and the blood treatment device.

42. The apparatus of claim 18, wherein said first value, related to the first pressure pulsation value, is an amplitude of the arterial blood pressure and said second value, related to the second pressure pulsation value, is an amplitude of the venous blood pressure.

43. The apparatus of claim 42, wherein the step of relating the first value and the second value includes obtaining a ratio between the first value and the second value and comparing said ratio with the threshold value to obtain a datum representing a state of partial or total occlusion in the blood line of the extracorporeal blood treatment circuit.

44. A method to detect partial or total occlusions of a blood line in an extracorporeal blood treatment apparatus, the method comprising:

determining a first pressure pulsation value in the blood line at a withdrawal portion of the blood line receiving arterial blood withdrawn from a patient, wherein the arterial blood is subject to a pulsating thrust due to a beating heart of the patient and the pressure pulsation value indicates a pressure variation due to the pulsating thrust, wherein the determination of the first pressure pulsation value includes acquiring successive first pressure values from a first pressure sensor monitoring the withdrawal portion of the blood line, and comparing the acquired successive first pressure values to determine the first pressure pulsation value;

determining a second pressure pulsation value in the blood line at an infusion portion of the blood line returning venous blood to the patient, wherein the second pressure pulsation value is sensed and acquired within a certain temporal interval during which the first pressure pulsation value is sensed and acquired;

comparing the first pressure pulsation value to the second pressure pulsation value; and emitting a signal representing a partial or total occlusion in the blood line in response to the comparison.

* * * * *